(12) United States Patent
Lyons (10) Patent No.: US 7,461,751 B2
(45) Date of Patent: Dec. 9, 2008

(54) SURGICAL STANDS, SURGICAL INSTRUMENT ORGANIZER ASSEMBLIES, AND METHODS OF USE THEREFOR

(76) Inventor: Diane C. Lyons, 1718 Auburn Ave. NW., Massillon, OH (US) 44647

( * ) Notice: Subject to any disclaimer, the term of this patent is extended or adjusted under 35 U.S.C. 154(b) by 0 days.

(21) Appl. No.: 11/775,311

(22) Filed: Jul. 10, 2007

(65) Prior Publication Data

US 2008/0011699 A1   Jan. 17, 2008

Related U.S. Application Data

(60) Provisional application No. 60/830,435, filed on Jul. 12, 2006.

(51) Int. Cl.
*A47F 7/00* (2006.01)
(52) U.S. Cl. .................... 211/85.13; 211/70.6
(58) Field of Classification Search .............. 211/70.6, 211/70.7, 60.1, 13.1, 175, 85.13; 422/50, 422/99, 297; 206/305, 372, 438; 248/127, 248/146, 37.3
See application file for complete search history.

(56) References Cited

U.S. PATENT DOCUMENTS

| | | | |
|---|---|---|---|
| 1,733,487 A * | 10/1929 | Hackley | 211/35 |
| 3,888,353 A * | 6/1975 | Leifheit | 211/37 |
| 4,229,420 A | 10/1980 | Smith et al. | |
| 4,342,391 A * | 8/1982 | Schainholz | 206/370 |
| 4,512,466 A | 4/1985 | Delang | |
| 4,641,749 A | 2/1987 | Link et al. | |
| 4,854,456 A * | 8/1989 | Lee | 211/14 |
| 4,865,821 A | 9/1989 | Langdon | |
| 5,046,624 A | 9/1991 | Murphy et al. | |
| 5,145,655 A | 9/1992 | Darlak | |
| 5,201,430 A | 4/1993 | Artzer | |
| 5,449,069 A * | 9/1995 | Pijanowski et al. | 206/370 |
| 5,664,691 A | 9/1997 | Boivin-Paradis | |
| 5,992,647 A * | 11/1999 | Malik | 211/34 |
| 6,048,503 A | 4/2000 | Riley et al. | |
| 6,367,637 B1 | 4/2002 | Davis et al. | |
| 6,915,912 B2 | 7/2005 | Davis et al. | |
| 2001/0035384 A1* | 11/2001 | Davis et al. | 211/85.13 |

* cited by examiner

*Primary Examiner*—Jennifer E. Novosad
(74) *Attorney, Agent, or Firm*—Ralph E. Jocke; Daniel D. Wasil; Walker & Jocke (57) ABSTRACT

An instrument stand for supportingly receiving surgical instruments is provided. The instrument stand includes at least one of an instrument support and a stabilization support, a first stand section and a second stand section. The second stand section is positionally coupled to the first stand section by at least one of the instrument support and the stabilization support. Also, a surgical instrument organizer assembly for supportingly receiving surgical instruments is provided, and includes an instrument stand and at least one clamp positionably coupled to the instrument stand. Further, a method of using a surgical instrument organizer assembly is provided.

20 Claims, 5 Drawing Sheets

SURGICAL STANDS, SURGICAL INSTRUMENT ORGANIZER ASSEMBLIES, AND METHODS OF USE THEREFOR

PRIORITY CLAIM

This application claims the benefit of the filing date of U.S. Provisional Patent Application Ser. No. 60/830,435, filed Jul. 12, 2006, for "Surgical Instrument Organization System," the contents of the entirety of which are incorporated herein by this reference.

FIELD OF THE INVENTION

The present invention relates generally to surgical instrument organization systems used in surgical settings to organize surgical instruments for reliable, rapid, ready access by medical personnel as needed during a surgical procedure and, more particularly, to surgical stands, surgical instrument organizer assemblies, and methods of use therefor.

BACKGROUND OF THE INVENTION

Surgical instruments anticipated as likely to be needed during any surgical procedure are conventionally assembled in advance of the surgery on a tray by, for example, a surgery technician or nurse. The tray is stably supported, such as along one side thereof, on rollers above the surgery floor in order to allow mobility and accessibility to the surgical instruments. The height of the tray above the surgery floor is such as to permit the tray to be selectively positioned at will over any portion of an occupied surgery bed, within easy reach of medical personnel. The tray, in combination with the support and rollers therefor, is conventionally referred to as a "mayo stand."

Various types of surgical instruments are routinely loaded onto a mayo stand in preparation for use in surgery. These surgical instruments are generally arranged on the mayo stand in a nesting, parallel relationship with the handles of the surgical instruments in alignment. In many cases, similar types of surgical instruments are grouped together and graded by size. Such a line up of surgical instruments is commonly known or referred to as a "stringer" or "stringer of surgical instruments." Examples of surgical instruments that would commonly be included in a stringer on a mayo stand include hemostats, tonsils, Haney clamps, and needle holders.

Known systems for organizing stringers on a mayo stand employ rolled cotton towels, foam organizers, and complicated metal structures. While the latter are occasionally capable, in addition, of securing a group of medical instruments together temporarily during sterilization in an autoclave, organization systems that employ towels or foam organizers cannot be so sterilized and are thus not reusable. Even metal organizers frequently lack the type of flexibility that would allow medical personnel in the surgical field to customize the organizer to accommodate various sizes of stringers or allow the metal organizers to adapt to various compositions of surgical instruments within a stringer.

Accordingly, there is an ongoing desire to provide a surgical stand capable of reuse after sterilization that accommodates various sizes of stringers or various compositions of surgical instruments within a striger. There is also a need to provide a surgical stand capable of adjustment to accommodate an assortment of surgical instruments while conserving space on a mayo stand. Further, there is a need for providing a reusable surgical stand having adjustable divisible sections for accommodating sets of stringers or stringer having different sized instruments. Further still, there is a need to provide a surgical stand capable of being stably repositionable about a mayo stand and un-affixed therefrom, in order to provide adaptable adjustability for sectionally supporting surgical instrument thereon Moreover, there is a need to provide a surgical stand that includes reusable adjustable dividers for receiving stringers of surgical instruments there between, particularly for providing sturdy upright support for the surgical instruments.

BRIEF SUMMARY OF THE INVENTION

In certain embodiments, an instrument stand is provided that may be reused after sterilization and advantageously accommodates various sizes of stringers and compositions of surgical instruments. The instrument stand is capable of adjustment allowing accommodation of an assortment of surgical instruments while efficiently conserving and utilizing space upon a mayo stand or other surface. Further, the reusable instrument stand includes adjustable or divisible sections for accommodating surgical instruments, stringers of surgical instruments, sets of stringers and stringers having different sized surgical instruments. Further still, the instrument stand may be stably repositioned about a mayo stand or other surface, allowing adaptable adjustability for sectionally supporting surgical instrument thereon or thereabout. Moreover, the instrument stand may receive reusable adjustable dividers, such as clamps, for receiving surgical instruments therebetween, while providing sturdy upright support for the surgical instruments.

In certain embodiments, an instrument stand for supportingly receiving surgical instruments is provided. The instrument stand includes at least one of an instrument support and a stabilization support, a first stand section and a second stand section. The second stand section is positionally coupled to the first stand section by at least one of the instrument support and the stabilization support.

In certain embodiments, a surgical instrument organizer assembly for supportingly receiving surgical instruments is provided. The surgical instrument organizer assembly includes an instrument stand and at least one clamp positionably coupled to the instrument stand.

A method of using a surgical instrument organizer assembly is also provided in accordance with an embodiment of the invention.

Other advantages and features of the present invention will become apparent when viewed in light of the detailed description of the various embodiments of the invention when taken in conjunction with the attached drawings and appended claims.

BRIEF DESCRIPTION OF THE DRAWINGS

While the specification concludes with claims particularly pointing out and distinctly claiming that which is regarded as the invention, the advantages of this invention may be more readily ascertained from the following description of the invention when read in conjunction with the accompanying drawings in which:

DETAILED DESCRIPTION OF THE INVENTION

Figure 1:
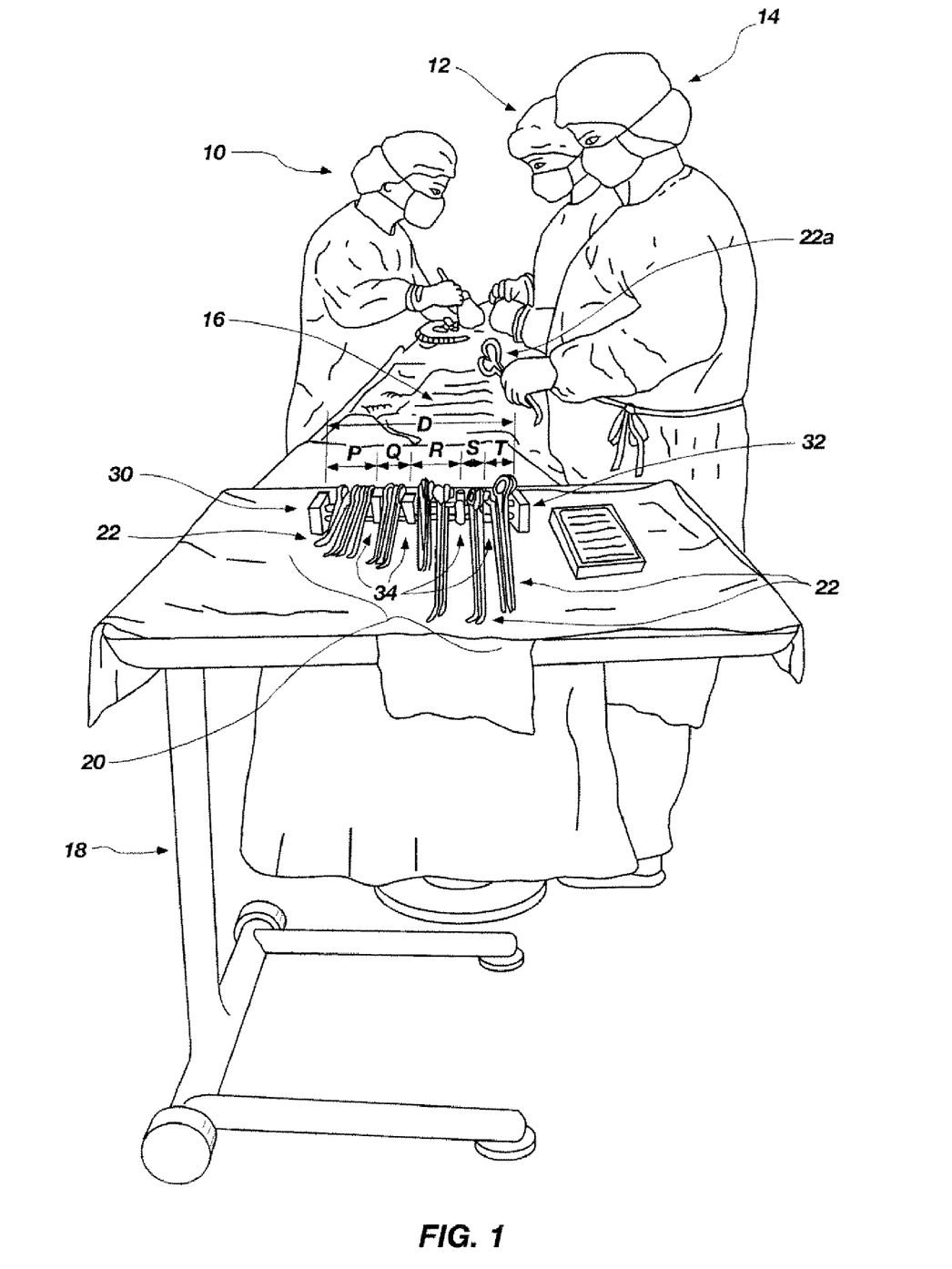
FIG. 1 is a perspective view of a mayo stand positioned over the foot of a surgery bed and loaded with surgical instruments in a stringer arrangement that are thus upheld for ready access by an embodiment of a surgical instrument organizer assembly in accordance with the invention.

FIG. 1 illustrates a surgical setting in which a surgical instrument organization system, or surgical instrument organizer assembly 30 is used to advantage. Shown, a doctor 10, a first assistant 12, and a nurse 14 are grouped about a surgical table upon which a prone patient 16 is undergoing a surgical procedure. Positioned over the surgical table at the foot of the patient 16 is a mayo stand 18 upon which a stringer 20 arrangement of surgical instruments 22 are organized upon the surgical instrument organizer assembly 30 and positionally upheld for ready use. The nurse 14 is shown in the process of removing a surgical instrument 22a from the surgical instrument organizer assembly 30 and passing the instrument 22a to the assistant 12.

The surgical instrument organizer assembly 30 includes an instrument stand 32 and at least one clamp 34. In this embodiment of the invention, four clamps 34 are shown separating, organizing and supporting the stringer 20 of surgical instruments 22.

Figure 2:
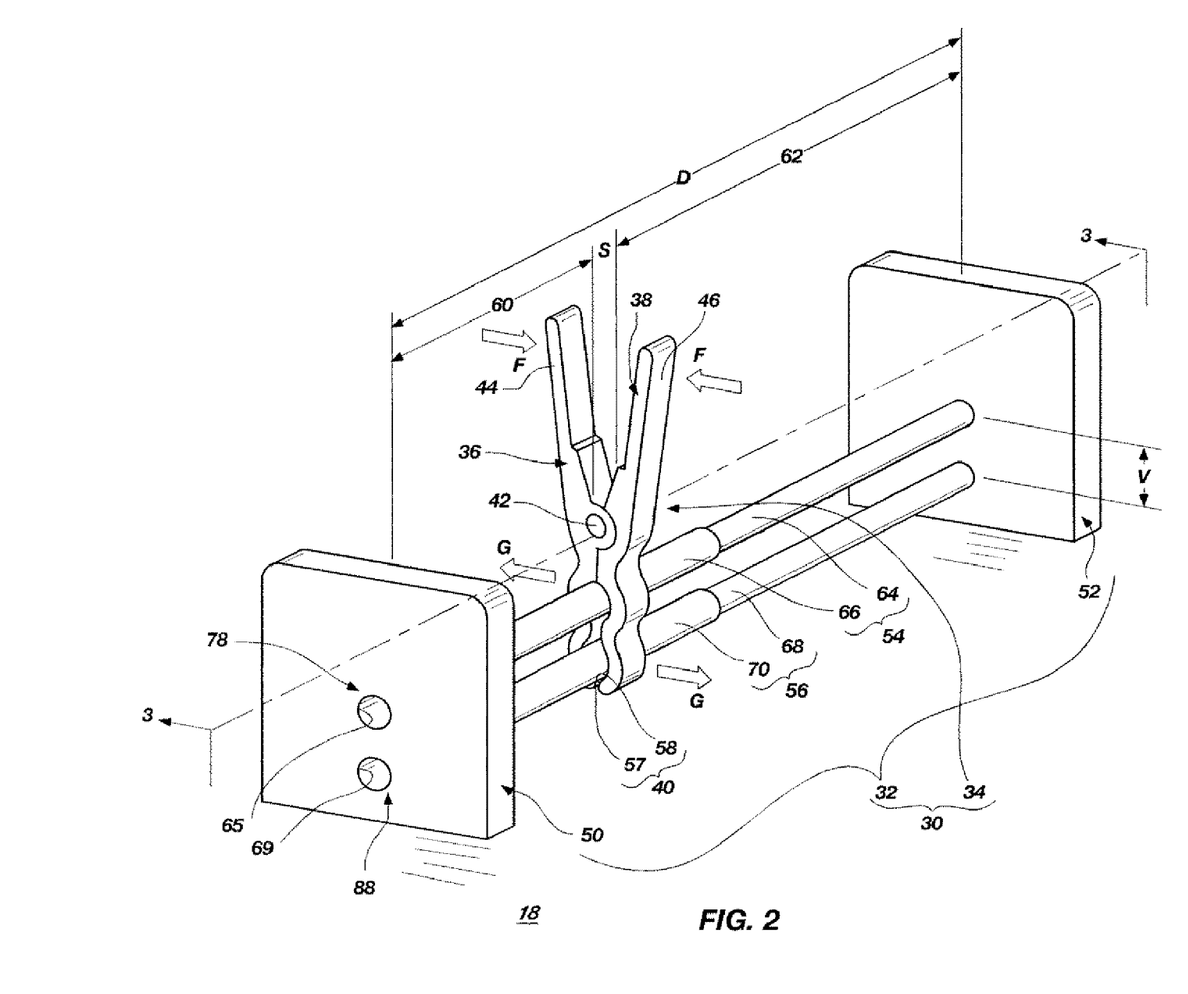
FIG. 2 is an enlarged perspective view of the surgical instrument organizer assembly of FIG. 1 empty of surgical instruments.
Figure 5:
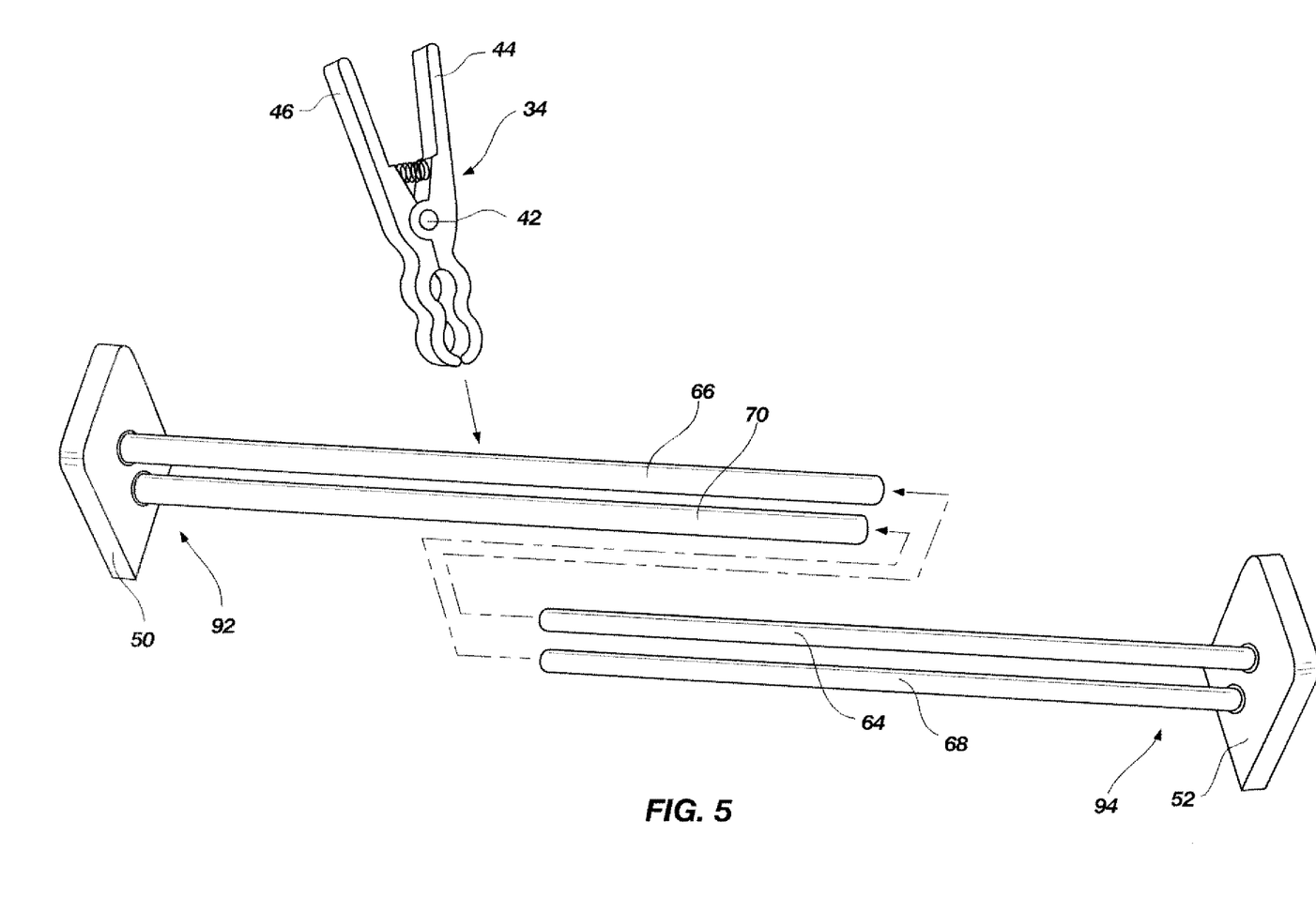
FIG. 5 shows assembly view of an instrument stand and a clamp of the surgical instrument organization system of FIG. 2.

As illustrated in FIG. 2, surgical instrument organizer assembly 30 includes an instrument stand 32 (hereinafter "stand") and one clamp 34. Reference may also be made to FIG. 5 which shows the clamp 34 disassembled from the stand 32, which is also disassembled into its constituent parts for sterilization.

The clamp 34 is generally nondestructively removably secured to stand 32 at a pre-selected location along a length D thereof by the nurse, assistant or doctor, as mentioned herein. While one clamp 34 is illustrated in FIG. 2, any desired number of clamps, such as the clamp 34, may be used with a stand, such as instrument stand 32, in the surgical instrument organizer assembly 30 configured according to embodiments of the invention.

The clamp 34 includes a pair of similarly-sized, elongated first and second arms 36, 38, respectively that meet at one end of clamp 34 to form a jaw 40 thereof. The first arm 36 and the second arm 38 are secured to each other at a shared medial location by a spring-loaded hinge 42 that urges the first arm 36 and the second arm 38 into the closed condition of the clamp 34 shown with the jaw 40 of the clamp 34 selectively clasping the stand 32. Nonetheless, the first arm 36 and the second arm 38 engage in relative pivoting movement out of the closed position of the clamp 34, when the biasing effect of the hinge 42 is overcome by sufficient counteracting force applied between the first arm 36 and the second arm 38.

Accordingly, the end of the first arm 36 on the opposite side of the spring-loaded hinge 40 from the jaw 40 is formed into a first handle 44, while the end of the second arm 38 on the opposite side of the hinge 40 from the hinge 40 is formed into a second handle 46. When a force F is applied by the fingers of a medical practitioner to the first handle 44 and to the second handle 46 in the directions indicated by correspondingly labeled arrows in FIG. 2, the jaw 42 opens in the manner indicated by arrows G allowing the grip of the jaw 40 to be released from the stand 32. According to the needs of medical personnel, the clamp 34 may then be repositioned at a different location along the length of the stand 32, or removed entirely from the stand 32 and thus, from the surgical instrument organization system 30. While a clamp 34 is biased about the hinge 40 by a spring, it is recognized that the clamp 34 may or may not have a biasing member. Furthermore, the clamp 34 may include a tension or compression member for supplying the requisite clamping force to secure the clamp 34 to the instrument stand 32.

The structure of the stand 32 will be investigated in detail by reference first to FIG. 2. The remote ends of the stand 32 includes a first footing 50 and a second footing 52 that support the stand 32 on the upper surface of the mayo stand 18 when the surgical instrument organizer assembly 30 is assembled thereupon with a stringer of surgical instruments in preparation for surgery. Extending between and upheld by the first footing 50 and the second footing 52 are an elongated instrument support 54 and therebelow, at a height H above the upper surface of the mayo stand 18, a stand stabilization shaft or support 56.

Advantageously, the instrument support 54 and the stabilization shaft 56 of the stand 32 allow the jaw 40 of the clamp 34 to grippingly supported in the closed condition thereof. Toward that end, the opposed faces 57, 58, of the jaw 40 may be configured as shown in FIG. 2 to conform closely to the exterior profile and the vertical separation V between the instrument support 54 and the stabilization shaft 56.

When thusly employed as part of the surgical instrument organizer assembly 30, the clamp 34 separates the distance D between the first footing 50 and the second footing 52 into a first instrument disposition slot 60 adjacent to first footing 50 and a second instrument disposition slot 62 adjacent to the second footing 52. The first instrument disposition slot 60 is as a result separated from the second instrument disposition slot 62 by a distance S representing the width of the clamp 34 as measured parallel to the hinge 42, the instrument support 54, and the stabilization shaft 56.

The use with the stand 32 of additional clamps, such as the lamp 34, will serve to further subdivide the distance D into additional and smaller instrument disposition slots along the length of the stand 32. In FIG. 1, for example, the surgical instrument organizer assembly 30 is shown to employ four clamps 34, thus subdividing the distance D between the first footing 50 and the second footing 52 into five distinct instrument disposition slots P, Q, R, S, T, along the length of the stand 32. The sizes of instrument disposition slots P, Q, R, S, T, can be varied at will by medical personnel according to the positions chosen selectively therefor, for each of the clamps 34.

Figure 3:
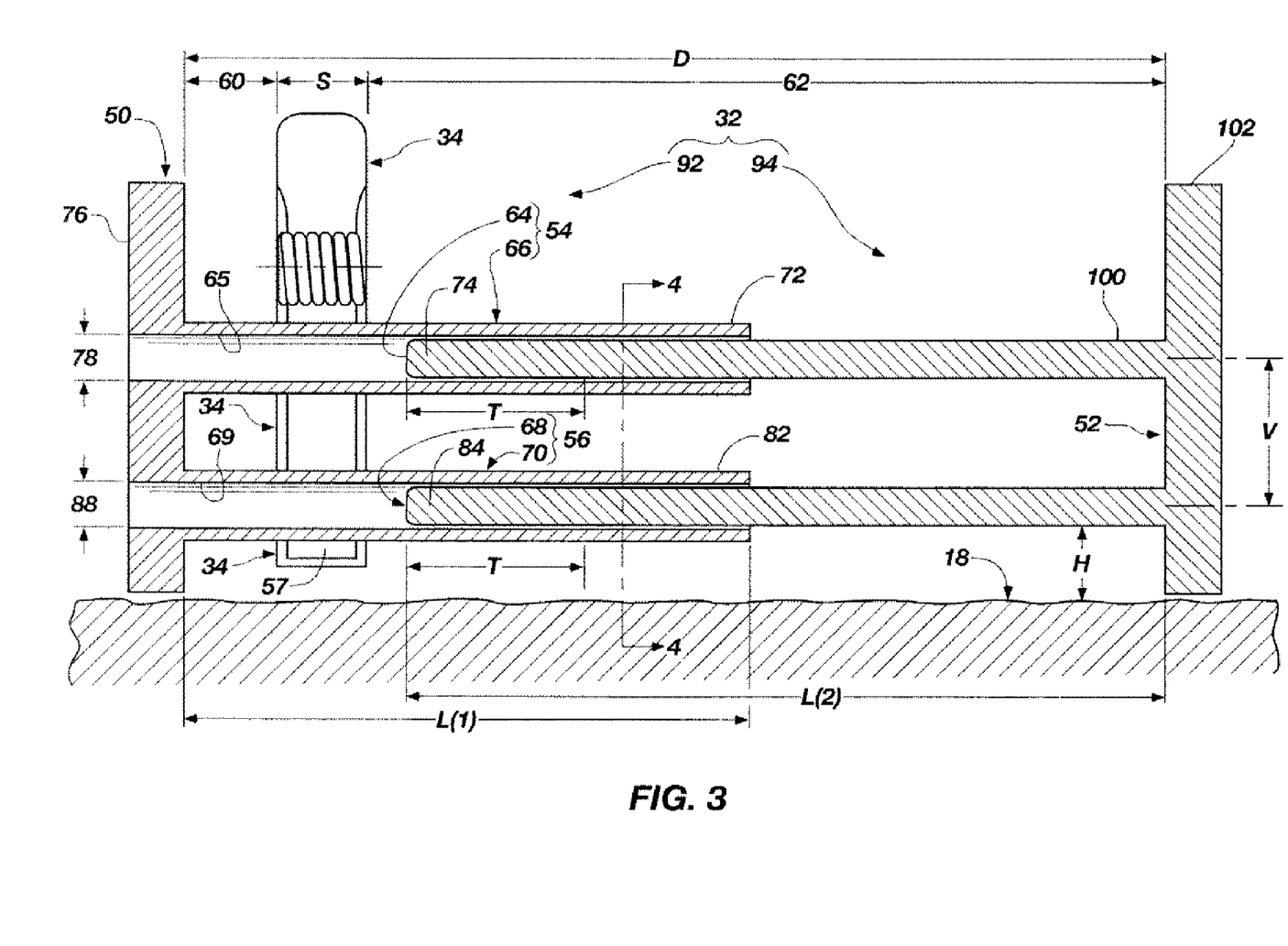
FIG. 3 is a cross-sectional elevation view of the surgical instrument organizer assembly of FIG. 2 taken along section line 3-3 shown therein.

As shown in FIG. 3, each of the instrument support 54 and the stabilization shaft 56 is a telescoping structure of an inner rod 64, 68 that is slidably longitudinally received within a hollow outer rod 66, 70, respectively. Thus, the inner support rod 64 is cantilevered from the second footing 52 and slidably disposed within a longitudinally extending interior passageway 65 in the hollow outer support rod 66 that projects from the first footing 50 to produce the instrument support 54. Similarly, the inner stabilization rod 68 is slidably disposed within a longitudinally extending interior passageway 69 in the hollow outer stabilization rod 70 that projects from the first footing 50 to produce the stabilization shaft 56.

To avoid the inclusion of problematic dead end spaces within the components described herein of the stand 32, the interior passageway 65 in the outer support rod 66 and the interior passageway 69 in the outer stabilization rod 70 open at both ends to the exterior of the stand 32. Thus, while the end of the interior passageway 65 at the free end 72 of the outer support rod 66 actually receives the free end 74 of the inner support rod 64, the opposite end of the interior passageway 65 opens through the first footing 50 on the face 76 thereof, opposite from the outer support rod 66 in an upper clean out aperture 78. Similarly, the end of the interior passageway 69 at the free end 82 of outer support rod 70 receives free end 84 of the inner support rod 68, and the opposite end of the interior passageway 69 also opens through the first footing 50 on the face 76 in a lower clean out aperture 88.

By means of this arrangement of components, the first footing 50 with the outer support rod 54 and the outer stabilization rod 70 projecting therefrom is slidable at will toward or away from the second footing 52 with the inner support rod 64 and the inner stabilization rod 68 projecting therefrom. Advantageously, the stand 32 may be increased or decreased in length, thus rendering distance D between the first footing 50 and the second footing 52 variable at the convenience of a user of the surgical instrument organizer assembly 30.

As shown in FIG. 3, the outer support rod 54 and the outer stabilization rod 70 have a first common length L(1), while the inner support rod 64 and the inner stabilization rod 68 have a second common length L(2). In those terms, the maximum length achievable for distance D between the first footing 50 and the second footing 52 by sliding the first footing 50 and the second footing 52 away from each other would be equal to the combination of the first common length L(1) plus the second common length L(2). Upon extension to the maximum length (L(1)+L(2)), the stand 32 would be separatable into a first stand half or section 92 made up of the first footing 50, the outer support rod 54 aid the outer stabilization rod 70, and a second stand half or section 94 made up of the second footing 52, the inner support rod 64 and the inner stabilization rod 68.

To forewarn a user of the stand 32 hat further movement of the first stand section 92 apart from the second stand section 94 risks disassembly of the stand 32, the surface of the inner support rod 64 for a distance T adjacent to the free end 74 thereof and the surface of the inner stabilization rod 68 for a distance T adjacent to the free end 84 thereof may be colored, textured, or coated in a manner that contrasts visually with the balance of the surface of the inner support rod 64 and the inner stabilization rod 86, respectively. When these visually contrastingly potions of the inner support rod 64 and the inner stabilization rod 86 present, respectively, at the free end 72 of the outer support rod 66 and at the free end 82 of the outer stabilization rod 70, a user is advised sensorially, such as visually, that the fullest extension of the stand 32 is being approached.

Disassembly of the stand 32 into the first stand section 92 and the second stand section 94, and unclamping all clamps 34 there from, facilitate sterilization, as illustrated in FIG. 5. Optionally, disassembly provides the opportunity to pass any of the free ends of any of the inner support rod 64, the outer support rod 66, the inner stabilization rod 68, or the outer stabilization rod 70 through apertures in handles of surgical instruments. Reassembling the first and the second section 92, 94, with the inner support rod 64, the outer support rod 66, the inner stabilization rod 68, or the outer stabilization rod 70 passing through the apertures in the handles of surgical instruments captures those surgical instruments as a group with the stand 32, whereupon the assembly may be manipulated as a unit for sterilization, transport, or other organizational purposes. However, it is conventionally recognized that a stringer wire (not shown) is customarily utilized to capture the above mention surgical instruments creating a stringer suitable for sterilization, transport, or utilization with embodiments of the invention mentioned herein.

It may be convenient, but not necessary, that the first common length L(1) of the outer support rod 54 and the outer stabilization rod 70 is equal to the second common length L(2) of the inner support rod 6 and the inner stabilization rod 68.

Where, as illustrated in FIG. 3, the ends of both the outer support rod 66 and the outer stabilization rod 70 adjacent to the first footing 50 are closed off, the minimum length achievable for distance D between the first footing 50 and the second footing 52 by sliding the first footing 50 and the second footing 52 toward each other is equal to the first common length L(1) of the outer support rod 66 and the outer stabilization rod 70 when the second common length L(2) is equal to or less than the first common length L(1). When the first common length L(1) the outer support rod 66 and the outer stabilization rod 70 is less than the second common length L(2) of the inner support rod 64 and the inner stabilization rod 68, then the distance D between the first footing 50 and the second footing 52 is minimized at the second common length L(2) when closed off; and is further minimized at the first common length L(1) when the free end 74 of the inner support rod 64 extends towards or from the face 76 of the first footing 50 through the upper clean out aperture 78, and the free end 84 of the inner stabilization rod 68 extends towards or from the face 76 of the first footing 50 through the lower clean out aperture 88.

Furthermore, if the end of either the outer support rod 54 and the outer stabilization rod 70 adjacent to the first footing 50 is closed off, then the minimum length achievable for distance D between the first footing 50 and the second footing 52 by sliding the first footing 50 and the second footing 52 toward each other is equal to the larger of the first common length L(1) of the outer support rod 66 and the outer stabilization rod 70 and the second common length L(2) of the inner support rod 64 and the inner stabilization rod 68.

Optionally, either of the inner support rod 64 and the inner stabilization rod 68 may be fabricated as hollow, tubular structures are contemplated within embodiments of the invention.

Figure 4:
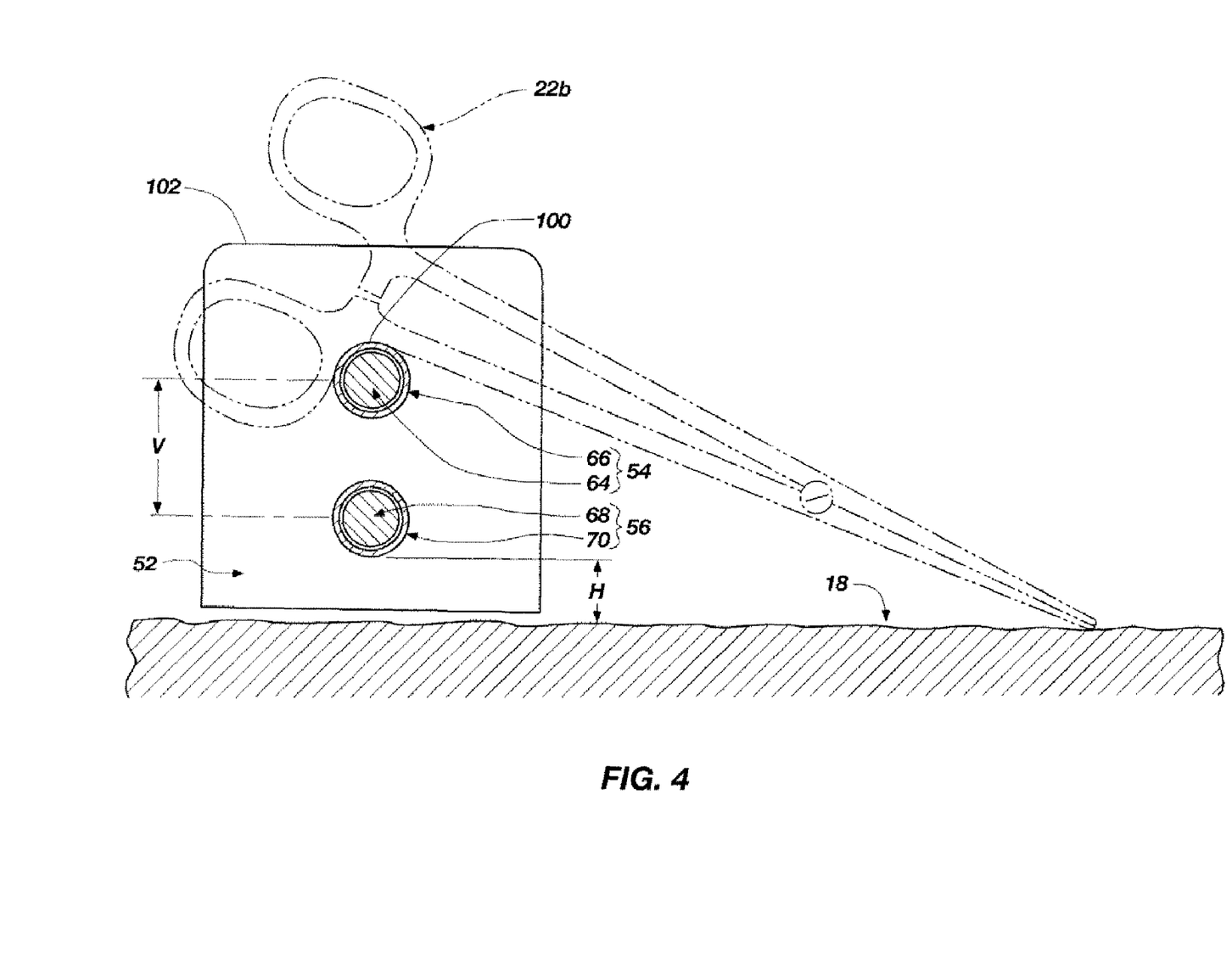
FIG. 4 is a cross-sectional elevation view an instrument stand of the surgical instrument organizer assembly of FIG. 3 taken along section line 4-4 shown therein.

As appreciated by reference to the transverse cross sections shown in FIG. 4, each of the inner support rod 64, the outer support rod 66, the inner stabilization rod 68, and the outer stabilization rod 70 has a circular outer profile. It is recognized that other shapes of outer profiles in these rods 64, 66, 68, 70 of the stand 32 may be desirable and workable in other embodiments of the invention. In still another aspect of the invention, the cross-sectional size and outer profile of the inner support rod 64 and the inner stabilization rod 68 relative to the cross-sectional size of the interior passageway 65 in the outer support rod 66 and the interior passageway 69 in the outer stabilization rod 70 be such as to permit the inner support rod 64 and the inner stabilization rod 68 to be slidably receivable along the interiors 65, 69 of the outer support rod 66 and the outer stabilization rod 70, respectively. In this regard, a close positionally engaging fit, e.g. sliding fit, is recommended between constituent rods, however, a lose or snug fit may be used to advantage.

Further, as shown in FIG. 4 the cross-sectional size and outer profile of the outer support rod 66 and the outer stabilization rod 70 are shown to be approximately equal. It is recognized that the outer support rod 66 and the outer stabilization rod 70 may have different sizes. It may, for example, be desired in enhancing the structural strength of the stand 32 to make the cross-sectional size and outer profile of the outer stabilization rod 70 large, or even substantially larger than the cross-sectional size and outer profile of the outer support rod 66. Corresponding adjustments to the cross-sectional size and outer profiles of the inner support rod 64 and the inner stabilization rod 68 may be desired to maintain relative slidability between the first stand section 92 and the second stand section 94, of the stand 32.

Furthermore, the relative positioning of the instrument support 54 and the stabilization shaft 56 need not be only as shown in FIG. 4. The instrument support 54 and the stabilization shaft 56 may be offset horizontally, or separated vertically to a greater or a lesser extent than depicted. It is advisable in some embodiments of the invention, that a top surface 100 of the instrument support 54 be located sufficiently below an upper edge 102 of, for example, the second footing 52 as to enable a surgical instrument, such as surgical instrument 22b shown in phantom in FIG. 4, to be rested on the top surface 100 of the instrument support 54 and leaned stably against, for example, a portion of the second footing 52 thereabove.

It is further recognized that neither it is necessary that, as illustrated herein, the outer telescoping port ions of both the instrument support 54 and the stabilization shaft 56 project from a single one of the first or the second footings 50, 52, respectively. One such outer telescoping portion could project from one of the first or the second footings 50, 52, while the other of the outer telescoping portions projects from the other of the first and the second footings 50, 52, respectively. Corresponding compensatory structural changes in the manner of supporting the inner of the telescoping portions of the instrument support 54 and the stabilization shaft 56 would produce an effective, functioning stand, like the stand 32. Moreover, the instrument support 54 of the stand 32 may replace the stabilization shaft 56 or the stabilization shaft 56 may replace the instrument support 54. Also, either of the instrument support 54 and the stabilization shaft 56 may be omitted from the stand. Moreover, additional instrument supports and stabilization shafts may be included with the stand 32.

The entirety of surgical instrument organizer assembly 30, including all components of each of the stand 32 and clamps 34, may be fabricated from durable, heat and moisture resistant materials that are medically sterilizeable and advantageously permit the surgical instrument organizer assembly 30 to be reusable in subsequent surgical procedures. Materials suitable for the surgical instrument organizer assembly 30 may include stainless steel, autoclavable plastics, and any other autoclavable materials in any combination suitable for assembly as shown and taught herein. It is recognized that the surgical instrument organizer assembly 30, including all components of each of the stand 32 and clamps 34, may as an assembly, or individually, be made of materials that are suitable for use in surgical procedures and may be either reusable or disposable.

In certain embodiments of the invention, the instrument stand may be a non-adjustable stand 32 having a first footing 50 and a second footing 52 separated by at least one of an instrument support 54 and the stabilization support 56.

While particular embodiments of the invention have been shown and described, numerous variations and other embodiments will occur to those skilled in the art, Accordingly, it is intended that the invention be limited in terms of the appended claims.

What is claimed is:

1. A method of using a surgical instrument organizer assembly adapted to supportingly receive surgical instruments, the method comprising:

(a) placing a reusable surgical instrument support stand of the assembly upon a surface, wherein the stand is adapted to be assembled and disassembled, wherein the stand when assembled is configured to support surgical instruments, wherein the stand when disassembled facilitates medical sterilization,
  wherein the stand includes a first end foot,
  wherein the stand includes a second end foot,
    wherein the second end foot includes a clean-out aperture,
  wherein the stand includes a length-adjustable surgical instrument support,
    wherein the support includes a shaft segment connected to the first end foot,
    wherein the support includes a hollow segment connected to the second end foot,
      wherein the hollow segment comprises an axis,
      wherein the hollow segment comprises an axially elongated hollow portion,
        wherein the hollow portion is axially aligned with the clean-out aperture,
      wherein the hollow segment comprises an inner surface configuration,
      wherein the hollow segment comprises an outer surface configuration,
        wherein the outer surface configuration includes an upper outer surface and a lower outer surface,
        wherein the lower outer surface is opposed of the upper outer surface along a straight line extending through the axis of the hollow segment,
      wherein the hollow segment is configured to telescopically slidably receive the shaft segment in the hollow portion; and (b) removably fastening at least one clamp of the assembly to the hollow segment, wherein the at least one clamp includes a first clamp fastened to the hollow segment, wherein the first clamp includes two pivotally attached clamp arms,
  wherein the clamp arms comprise opposed jaw ends,
    wherein each jaw end comprises a jaw face,
      wherein each jaw face includes a curved clamp arm end tip,
  wherein the clamp arms comprise opposed handle ends,
    wherein the handle ends are manually pivotable relative to each other enabling the jaw ends to be moved between a hollow segment fastening position and an open jaw position,
      wherein in the hollow segment fastening position
        the handle ends are positioned beyond the upper outer surface,
        the jaw faces form an inner configuration that substantially corresponds to the outer surface configuration,
        the curved clamp arm end tips extend beyond the lower outer surface,
        the first clamp is prevented from rotating relative to the hollow segment, and
        the first clamp separates the stand into medical instrument disposition slots,
      wherein in the open jaw position the first clamp is removable from the hollow segment.

2. The method according to claim 1, wherein step (a) includes at least one of adjusting or positioning the surgical instrument support to a select length while placing the stand upon the surface.

3. The method according to claim 1 wherein the shaft segment has located thereon at a predetermined distance from a free end thereof, a fully-extended visual warning indicator, and further comprising (c) telescopically sliding the shaft segment relative to the hollow segment.

4. The method according to claim 1, and further comprising
(c) placing and supporting one or more surgical instruments upon the surgical instrument support in one or more of the medical instrument disposition slots.

5. The method according to claim 1 wherein the surgical instrument support includes a first axis, wherein the stand includes a stabilization support, wherein the stabilization support includes a second axis substantially parallel to and spaced from the first axis, wherein the stabilization support includes a stabilization shaft segment connected to the first end foot, wherein the stabilization support includes a stabilization hollow segment connected to the second end foot, wherein the stabilization hollow segment is configured to telescopically slidably receive the stabilization shaft segment, and further comprising
(c) telescopically sliding the stabilization shaft segment relative to the stabilization hollow segment.

6. The method according to claim 5 wherein step (b) includes removably fastening the first clamp to both the surgical instrument support and the stabilization support.

7. A surgical instrument organizer assembly adapted to supportingly receive surgical instruments, including:
a reusable surgical instrument support stand,
wherein the stand is adapted to be assembled and disassembled, wherein the stand when assembled is configured to support surgical instruments, wherein the stand when disassembled facilitates medical sterilization,
wherein the stand includes a first end foot,
wherein the stand includes a second end foot,
wherein the second end foot includes a clean-out aperture,
wherein the stand includes a length-adjustable surgical instrument support,
wherein the support includes a shaft segment connected to the first end foot,
wherein the support includes a hollow segment connected to the second end foot,
wherein the hollow segment comprises an axis,
wherein the hollow segment comprises an axially elongated hollow portion,
wherein the hollow portion is axially aligned with the clean-out aperture,
wherein the hollow segment comprises an inner surface configuration,
wherein the hollow segment comprises an outer surface configuration,
wherein the outer surface configuration includes an upper outer surface and a lower outer surface,
wherein the lower outer surface is opposed of the upper outer surface along a straight line extending through the axis of the hollow segment,
wherein the hollow segment is configured to telescopically slidably receive the shaft segment in the hollow portion,
at least one clamp removably fastened to the hollow segment, wherein the at least one clamp includes a first clamp fastened to the hollow segment,
wherein the first clamp includes two pivotally attached clamp arms,
wherein the clamp arms comprise opposed jaw ends,
wherein each jaw end comprises a jaw face,
wherein each jaw face includes a curved clamp arm end tip,
wherein the clamp arms comprise opposed handle ends,
wherein the handle ends are manually pivotable relative to each other enabling the jaw ends to be moved between a hollow segment fastening position and an open jaw position,
wherein in the hollow segment fastening position
the handle ends are positioned beyond the upper outer surface,
the jaw faces form an inner configuration that substantially corresponds to the outer surface configuration,
the curved clamp arm end tips extend beyond the lower outer surface,
the first clamp is prevented from rotating relative to the hollow segment, and
the first clamp separates the stand into medical instrument disposition slots,
wherein in the open jaw position the first clamp is removable from the hollow segment.

8. The surgical instrument organizer assembly of claim 7, wherein the at least one clamp is positionably coupled to the instrument stand at a pre-selected location along a length of the instrument stand.

9. The surgical instrument organizer assembly of claim 8, wherein the first clamp comprises a biasing spring, a first arm and a second arm, wherein the first arm is pivotally coupled to the second arm about a hinge enabling the biasing spring to provide retention forces between the first arm and the second arm, wherein the first arm and the second arm form a jaw.

10. The surgical instrument organizer assembly of claim 9, wherein the first arm comprises a first handle and the second arm comprises a second handle, wherein the first handle and the second handle are pivotally aligned about an axis of the hinge allowing the jaw to extend openly when the first handle and the second handle are retracted together about the hinge.

11. The surgical instrument organizer assembly of claim 7 wherein the shaft segment has located thereon at a predetermined distance from a free end thereof, a fully-extended visual warning indicator.

12. The surgical instrument organizer assembly of claim 7, wherein the at least one clamp comprises a plurality of clamps positionably coupled to and separating the instrument stand into a plurality of instrument disposition slots.

13. The surgical instrument organizer assembly of claim 12, wherein the plurality of clamps comprises four clamps separating the instrument stand into five distinct instrument disposition slots.

14. The surgical instrument organizer assembly of claim 7 wherein the surgical instrument support includes a first axis,
wherein the stand includes a stabilization support,
wherein the stabilization support includes a second axis substantially parallel to and spaced from the first axis,
wherein the stabilization support includes a stabilization shaft segment connected to the first end foot,
wherein the stabilization support includes a stabilization hollow segment connected to the second end foot,
wherein the stabilization hollow segment is configured to telescopically slidably receive the stabilization shaft segment.

15. The surgical instrument organizer assembly of claim 14 wherein the clean-out aperture comprises a first clean-out aperture, wherein the second end foot includes a second clean-out aperture, wherein the stabilization hollow segment comprises an axis, wherein the stabilization hollow segment comprises an axially elongated hollow portion, wherein the stabilization hollow portion is axially aligned with the second clean-out aperture.

16. The surgical instrument organizer assembly of claim 14 wherein the first clamp is removably fastened to both the surgical instrument support and the stabilization support.

17. The surgical instrument organizer assembly of claim 16 wherein the surgical instrument support is positioned relatively above the stabilization support, wherein the handle ends are positioned above the surgical instrument support, and wherein the curved clamp arm end tips extend below the stabilization support.

18. The surgical instrument organizer assembly of claim 16 wherein the jaw faces form two inner configurations, wherein a first inner configuration substantially corresponds to an outer surface configuration of the surgical instrument support, and wherein a second inner configuration substantially corresponds to an outer surface configuration of the stabilization support.

19. The surgical instrument organizer assembly of claim 16 wherein the at least one clamp comprises a plurality of clamps removably fastened to both the surgical instrument support and the stabilization support.

20. The surgical instrument organizer assembly of claim 7 wherein the at least one clamp comprises a plurality of clamps removably fastened to the hollow segment.

* * * * *